March 17, 1964 F. W. ANDERSON Plant Pat. 2,380
ALMOND TREE
Filed April 12, 1963
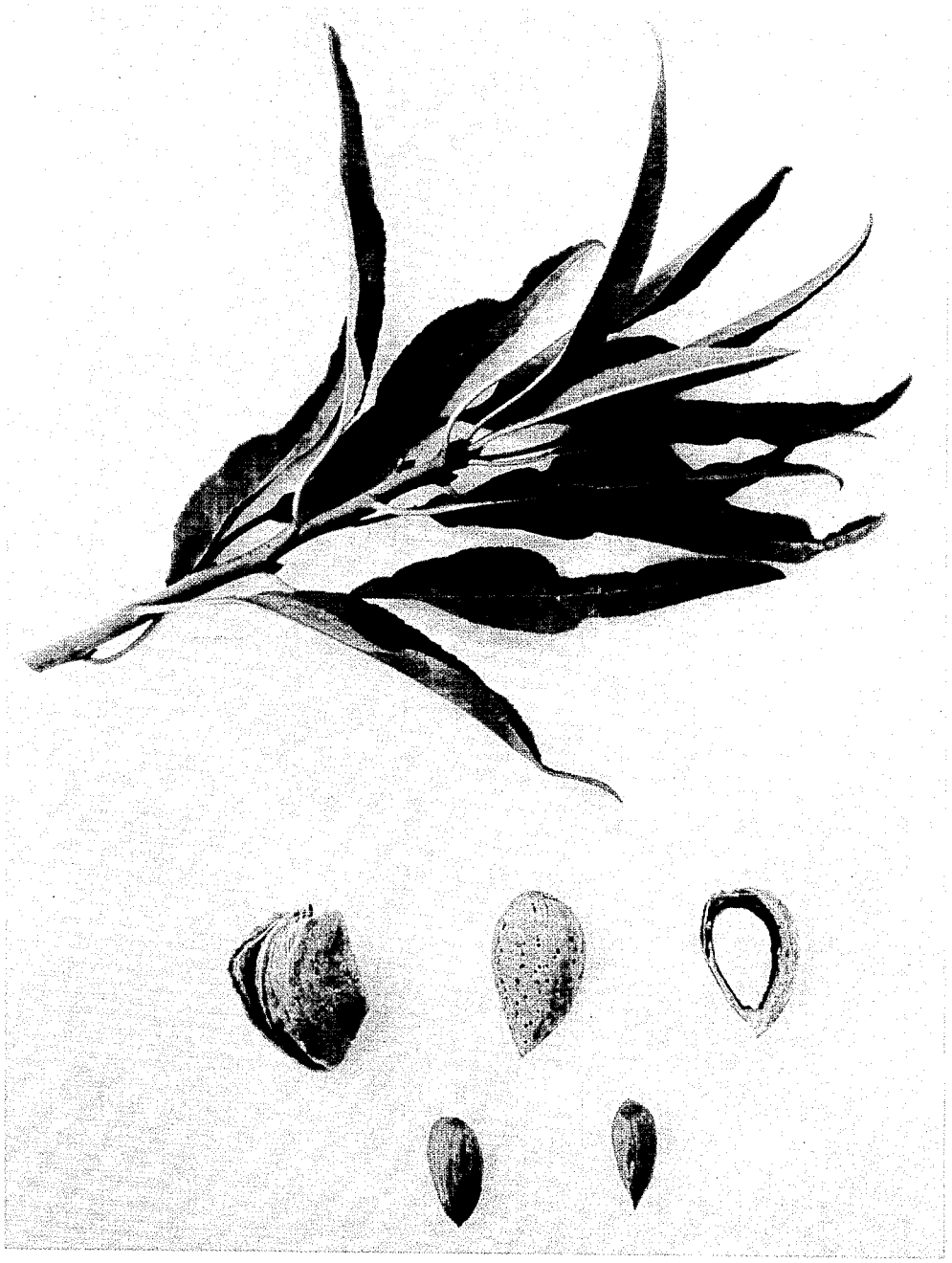
INVENTOR
*Frederic W. Anderson*
BY *Webster & Webster*
ATTYS.

United States Patent Office

Plant Pat. 2,380
Patented Mar. 17, 1964

2,380
ALMOND TREE

Frederic W. Anderson, Merced, Calif., assignor to Fowler Nurseries, Inc., Newcastle, Calif., a corporation of California Filed Apr. 12, 1963, Ser. No. 272,814
1 Claim. (Cl. Plt.—30)

This invention relates to a new and distinct variety of almond tree.

The variety is primarily characterized, as to novelty, by a vigorous tree that blooms heavily late in the season, followed by heavy crops of medium to small nuts which are harder and better sealed than the Nonpareil and with broader and more acceptable kernels for confections than the Mission.

The variety is further characterized by interfertility with the Nonpareil, Mission, Ruby (United States Plant Patent No. 1,698), and Emerald (United States Plant Patent No. 2,208); such interfertility being most desirable for a commercial variety of almond tree.

I originated the herein claimed variety of almond tree in my experimental nursery and orchard located near Le Grand, in the county of Merced, California, as a seedling resulting from a cross between the Mission as the seed parent and the Nonpareil as the pollen parent. A large number of test seedlings of such parentage were produced and grown under conditions of careful and continuing observation.

The present variety, which in general is intermediate in many characteristics betwen the Nonpareil and Mission, was selected from such test seedlings as having substantial commercial promise because of its late blooming period, high productivity of excellent nuts, and interfertility with a number of other varieties.

Subsequent to its origination and selection, I asexually reproduced the present variety of almond tree by topworking on mature trees in my orchard located as aforesaid; such asexual reproduction, in maturity, having run true to the parent in all respects.

The drawing comprises an illustration, by photographic reproduction in color, of a first year shoot with leaves; a nut with the hull thereon; a nut with the hull removed; a nut with half the shell removed and the kernel cut to expose the meat; a kernel from one side; and another kernel from one edge.

Referring now more specifically to the botanical details of this new and distinct variety of almond tree, the following is an outline description thereof; all major color plate identifications, by comparison with fresh specimens, being by reference to Maerz and Paul Dictionary of Color; except where common terms of color definition are employed:

Tree:
- *Density.*—Open.
- *Size.*—Medium.
- *Vigor.*—Vigorous.

Trunk: Form—medium.

Branches:
- *Form.*—Medium.
- *Texture.*—Medium.
- *Branching habit.*—Spreading.

Foliage: Quantity—medium to abundant.

Leaves:
- *Size.*—Medium. Average length—2⅞". Average width—13/16".
- *Shape.*—Ovate; acutely pointed.
- *Thickness.*—Medium.
- *Texture.*—Smooth.
- *Margin.*—Crenate.
- *Petiole.*—Length—medium. Thickness—slender.
- *Glands.* — Average number — two. Size — small. Position—alternate; on petiole, at base of blade.
- *Color.*—Topside—medium green (23–L–7). Underside—lighter green (22–L–5).

Bloom:
- *Amount of bloom.*—Heavy.
- *Color.*—White.
- *Blooming period.*—Late, usually opens with Mission or a day or two earlier, and lasts a day or two longer.

Crop:
- *Bearing.*—Regular bearer.
- *Productivity.*—Very heavy.
- *Distribution of nuts on tree.*—Well distributed.
- *Harvest period.*—Follows Nonpareil and before Mission.
- *Tenacity.*—Hangs well on tree; easy to harvest; easy to hull.

Hull:
- *Outer surface.*—Smooth.
- *Form.*—Regular.
- *Thickness.*—Thin.
- *Flesh.*—Tough.
- *Suture.*—Ridged.
- *Color.*—At harvest — gray green (15–E–1) with silvery sheen.
- *Dehiscence.*—Opens freely.
- *Splitting.*—Along suture.

Nut:
- *Size.*—Medium to small. Average length—1⅛". Average width—¾". Average thickness—⅝".
- *Nuts per ounce on average sample.*—16.
- *Form.*—Length/width — ovate. Width/thickness — medium.
- *Shell.*—Soft to hard; thick; smooth. Outer shell—hard. Inner shell—soft; well sealed.
- *Color.*—Medium tan (12–G–7).
- *Pits.*—Large; irregular.
- *Base.*—Square.
- *Stem scar.*—Large
- *Apex.*—Acute.
- *Wing.*—Narrow; thin.
- *Ventral streak.*—Light; broad; long; point acute.
- *Percentage of kernel to nut on average sample.*—50–55 percent.

Kernel:
- *Size.*—Medium to small. Average length—13/16". Average width—½". Average thickness—⅜".
- *Kernels per ounce on average sample.*—30.
- *Form.*—Length/width—oval; wedge. Width/thickness—medium to flat.
- *Base.*—Square to ventrally oblique.
- *Stem scar.*—Small.
- *Apex.*—Obtuse; blunt.
- *Surface.*—Smooth.
- *Pellicle.*—Thin.
- *Pubescence.*—Medium.

*Color.*—Medium light brown (14–L–12).
*Number of doubles.*—Few.
*Defective kernels.*—Very few.
*Flavor.*—Normal.
*Quality.*—Good.

Except where otherwise indicated, all of the herein identified existing varieties of almond tree are unpatented.

The tree and its nuts herein dscribed may vary in slight detail due to climatic and soil conditions under which this variety may be grown; the present description being of the variety as grown in the Central Valley of California.

The following is claimed:

A new and distinct variety of almond tree, substantially as illustrated and described, characterized by a vigorous tree blooming heavily late in the season, followed by the regular bearing of very heavy crops of medium to small nuts which are harder and better sealed than the Nonpareil and with broader kernels than the Mission; and further characterized by blooming with the Mission or a day or two earlier and lasting a day or two longer; and additionally characterized by a harvest period following the Nonpareil but before the Mission; the variety being interfertile with the Nonpareil, Mission, Ruby, and Emerald.

No references cited.